United States Patent [19]

Meyer

[11] Patent Number: 5,269,170
[45] Date of Patent: Dec. 14, 1993

[54] MEASURING SYSTEM AND PROCESS USING ZERO SHIFT COMPENSATION CIRCUIT

[75] Inventor: Emilio Meyer, Assago-Milano, Italy
[73] Assignee: Panametrics, Inc., Waltham, Mass.
[21] Appl. No.: 981,501
[22] Filed: Nov. 25, 1992
[51] Int. Cl.$^5$ ............................................ G01N 27/74
[52] U.S. Cl. ...................... 73/25.02; 324/204
[58] Field of Search ............................ 73/25.02, 25.01; 324/204

[56] References Cited

U.S. PATENT DOCUMENTS

| | | | |
|---|---|---|---|
| 2,565,230 | 8/1951 | Hebler | 73/25.2 |
| 2,693,103 | 11/1954 | Krupp | 73/25.2 |
| 2,759,354 | 8/1956 | Cherry et al. | 73/25.2 |
| 2,782,102 | 2/1957 | Howe | 324/703 |
| 2,944,418 | 7/1960 | Engelhardt | 73/25.2 |
| 2,951,359 | 9/1960 | Krupp | 73/25.2 |
| 3,064,465 | 11/1962 | Richardson | 73/25.2 |
| 3,184,954 | 5/1965 | Klein | 73/25.2 |
| 3,276,244 | 10/1966 | Wilson et al. | 73/25.2 |
| 3,292,421 | 12/1966 | Meyer | 73/25.2 |
| 3,435,662 | 4/1969 | Meyer | 73/25.2 |
| 3,616,679 | 11/1971 | Meyer et al. | 73/25.2 |
| 3,646,803 | 3/1972 | Meyer | 73/25.2 |
| 4,893,495 | 1/1990 | Meyer | 73/25.2 |
| 5,012,669 | 5/1991 | Meyer | 73/25.02 |

FOREIGN PATENT DOCUMENTS 64957 10/1946 Denmark .

OTHER PUBLICATIONS

Medlock et al., "Oxygen Analysis," Transactions of the Instruments and Methods Conference, Stockholm, 1949, pp. 1–8.
Ellis et al., "The Measurement of Gaseous Oxygen Tension Utilizing Paramagnetism," 40 British Journal of Anesthesia 569 (1968).
Transducer Interfacing Handbook, a guide to analog signal conditioning, Edited by Daniel H. Sheingold, Published by Analog Devices, Inc., Norwood, Massachusetts, Chapter 2, Bridges, pp. 31–43 (no date).
A. Verdin, Gas Analysis Instrumentation, Published by McMillan, Paramagnetic Oxygen Analyzers, pp. 49–66 (no date).
Gas Analysis by Measurement of Thermal Conductivity, H. A. Daynes, Cambridge University Press, Chapter 6, Design of the Resistance Bridge (no date).
C. C. Minter et al., Thermal Conductivity Bridge for Gas Analysis, Analytical Chemistry, vol. 23, No. 1, Jan. 1951.

*Primary Examiner*—Peter Kratz
*Attorney, Agent, or Firm*—Lahive & Cockfield

[57] ABSTRACT

A zero compensation circuit particularly is used in an oxygen sensing apparatus and method employing a sensing cell including two pairs thermistors and a source of an inhomogenous magnetic field. One thermistor of each pair is electrically heated and is positioned inside the magnetic field, and the second thermistor of each pair is positioned adjacent to the respective first thermistor of each pair, substantially outside the magnetic field. When oxygen is present in the sensing cell, the thermistors inside the magnetic field generate a gas flow in the direction of the adjacent thermistors of each pair positioned outside the magnetic field, thus tending to reduce the temperature of the thermistors inside the field and increase the temperature of the thermistors outside the field. The thermistors are connected in a measuring bridge circuit including elements for maintaining the temperature of the thermistors at a substantially constant level, thereby providing a signal that can be used to compensate for changes in the thermal characteristics of the background gases.

The zero compensation circuit is formed of an inner bridge used to null the effects of background gases on the oxygen measuring circuit. The bridge uses non-linear voltage limiting elements to allow for compensation of more than one background gas.

12 Claims, 2 Drawing Sheets

MEASURING SYSTEM AND PROCESS USING ZERO SHIFT COMPENSATION CIRCUIT

BACKGROUND OF THE INVENTION

This invention relates in general to circuitry useful in conjunction with Wheatstone Bridge measuring systems and more particularly, to an apparatus and method for measuring oxygen concentration in gas mixtures by magnetic means without incurring a substantial error due to paramagnetic or thermal properties of background gases.

Accurate measurement of oxygen concentration in a gas mixture is important in a wide range of industrial, clinical and laboratory processes. In response to this need, a variety of devices have been proposed or developed for measuring oxygen concentration. A characteristic of oxygen which is often exploited in these devices is that oxygen is paramagnetic, in that its molecules seek the strongest part of a magnetic field. Most other gases, in contrast, are diamagnetic, in that their molecules seek the weakest part of a magnetic field. This characteristic of oxygen has led to a number of methods and devices for measuring oxygen concentration in gas mixtures.

One type of apparatus for measuring the concentration of oxygen relies upon the inverse relationship between temperature and the magnetic susceptibility of oxygen. As a result of this inverse relationship, heating a portion of an oxygen-containing mixture in a non-homogenous magnetic field creates a "magnetic wind" effect, which can be measured through its thermal effect on an electrical resistance element. Various configurations of magnetic wind devices are discussed in Medlock, et al., "Oxygen Analysis," *Transactions of the Instruments and Methods Conference*, Stockholm, 1949, pp. 1–8; and Ellis, et al., "The Measurement of Gaseous Oxygen Tension Utilizing Paramagnetism," 40 *British Journal of Anesthesia* 569 (1968).

Conventional magnetic wind oxygen measurement devices, however, are subject to relatively large errors due to the changes in the thermal properties of the surrounding or "background" gases. In particular, the presence of different background gases causes conventional magnetic wind oxygen sensors to yield false readings of oxygen levels, due to the large differences in thermal characteristics of the background gases.

One type of measuring device, such as that described in U.S. Pat. No. 4,893,495, reduces these effects by nulling the contribution of a single background gas. In this device the measuring circuit is a Wheatstone bridge, which is zeroed for one background condition. In situations where the gas mixture has two or more background gases, this circuitry cannot be zero compensated for the additional background gas.

If, for example, a measurement of oxygen is required over a 0 to 1% range, in a gas stream consisting of nitrogen and oxygen in a conventional oxygen analyzer, the measuring bridge will be adjusted to yield a zero oxygen reading in the presence of 100% nitrogen. The conventional magnetic wind oxygen sensor will then provide correct oxygen measurements, within the limits of the overall analyzer accuracy, of any oxygen concentration within the measuring range of 0–1% oxygen.

If, however, nitrogen is replaced by propane, for example, without resetting the zero compensation, an error would result that is approximately 86% of scale. Although the error for other gases may not be of such magnitude, it can often be greater than tolerable. It will be understood then, that where the background gas mixture includes two or more gases and only one can have zero calibration, this type of error can result.

False readings of this type are not only inconvenient but also may be dangerous. A measuring device showing a falsely low oxygen content may fail to warn of a potentially explosive situation.

Accordingly, there exists a need for circuitry which can provide accurate and reliable measurement of one variable component in a medium, regardless of the concentration of background components of the medium.

It is another object of the invention to provide oxygen sensing methods and apparatus which yield accurate measurement of oxygen concentration, independent of background gas composition and thermal properties.

Other general and specific objects of the invention will in part be obvious and will in part appear hereinafter.

SUMMARY OF THE INVENTION

Broadly speaking, the present invention, provides apparatus for measuring the concentration of one component of a medium which includes additional background components. This is achieved by incorporating in a Wheatstone bridge circuit, a second bridge circuit which can be adjusted first to provide a zeroing calibration for one background component with only that component constituting the medium, and then can be separately adjusted to provide a zeroing calibration with only the second background component constituting the medium. With the variable component and the background components included in the medium to be measured, the bridge is maintained in balance by an application of a voltage signal across the primary arms of the bridge circuit with the value of this voltage then serving as an indication of the concentration of the variable component in the medium. In one embodiment of the invention, the apparatus includes magnetic field elements for generating an inhomogenous magnetic field, and at least one electrically heated magnetic wind generating thermistor having an electrical parameter proportional to concentration of a paramagnetic gas in the gas mixture.

The apparatus also includes at least one heat sensing thermistor having an electrical parameter proportional to temperature, positioned substantially outside the inhomogenous magnetic field. The sensing thermistor senses the magnetic wind generated by the magnetic wind generating thermistor in the presence of a paramagnetic gas, by sensing the heat transfer resulting from the magnetic wind.

The apparatus further includes signal generating elements in electrical circuit with the magnetic wind generating thermistor elements of the magnetic wind sensing thermistor elements. The signal generating elements measure an electrical parameter of the wind sensing thermistor and generate a measurement signal having an amplitude representative of the concentration of the paramagnetic gas in the gas mixture since it is proportional to the magnitude of the magnetic wind in the presence of the paramagnetic gas.

Typically, the signal generating elements include a constant temperature electrical bridge and a measurement electrical bridge, itself including a Wheatstone bridge. The temperature control elements include current control elements, responsive to electrical imbalance between the constant temperature electrical bridge and the measurement bridge. The constant temperature electrical bridge serves to control current to the Wheatstone bridge for maintaining the first and second magnetic wind sensing thermistors at a substantially constant temperature.

The measurement bridge includes the wind generating and wind sensing thermistors on one side and still another inner bridge on the other side. This inner bridge is for negating any contribution to the oxygen measurement due to thermal properties of a background gas.

The inner bridge comprises a Zener diode, a potentiometer and a fixed resistor in series on one side, and the same elements but in opposite order on the other side. The two potentiometers have their arms electrically connected through a third potentiometer.

Also, the measurement signal can be corrected in response to changes in background gases in the gas mixture, by generating correction signals representative of the electrical imbalance between the constant temperature electrical bridge and the measurement electrical bridge. These correction signals are combined with the measurement signal to compensate for changes in the thermal properties of background gases in the gas mixture.

While the invention, in a preferred embodiment, is described as applied to the measurement of oxygen concentration in a gas mixture, essentially due to changes in thermal conductivity of the gas by generation of magnetic winds in response to heat produced by heat generating thermistors, it is also applicable to other measurement problems. It can be applied, for example, to measuring a variable heat conductivity in a liquid mixture due to concentration of a specific liquid component in the presence of two background liquid components, providing that the effect of the background components is additive in nature. Similarly, this measuring circuit could be employed to measure the variation in the optical reflectance or transmission properties of a medium to variation of a specific component of the medium, employing light generation and light sensing components responsive to electrical currents.

BRIEF DESCRIPTION OF THE DRAWINGS

For a fuller understanding of the nature and objects of the invention, reference should be made to the following detailed description and the accompanying drawings, in which.

DESCRIPTION OF PREFERRED EMBODIMENTS

Figure 1:
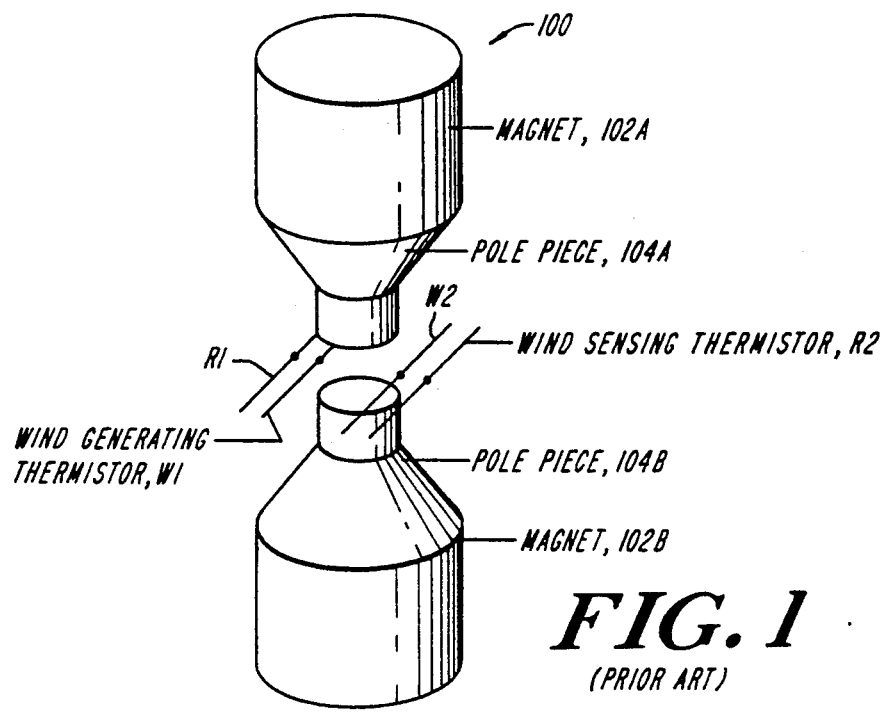
FIG. 1 is a schematic diagram depicting a prior art oxygen sensing cell employable in conjunction with the circuitry of this invention.

FIG. 1 is a schematic diagram depicting a configuration of an oxygen sensing cell known in the art, and described in U.S. Pat. No. 4,893,495, which is incorporated herein by reference. The oxygen sensor utilizes the "magnetic wind" phenomenon, and includes a sensor cell 100 having two pairs of thermistors R1, W1, and R2, W2. In the preferred embodiment, the thermistors are 2000 Ohm standard bead thermistors such as those sold by Fenwal Electronics.

One thermistor of each pair of thermistors is electrically heated, i.e. thermistors W1 and W2, and is located in a magnetic zone of high field intensity and magnetic field gradient. As illustrated in FIG. 1, for example, thermistors W1 and W2 are located between the pole pieces 104A and 104B of magnets 102A and 102B, respectively, where a high-intensity, non-uniform magnetic field is created. The second thermistor of each pair of thermistors, i.e. thermistors R1 and R2, is located adjacent to W1 and W2, respectively, but substantially outside the region of high magnetic field intensity.

When a gas is present in the oxygen sensing cell 100, and thermistors W1 and W2 are electrically heated, thermistors W1 and W2, referred to as the heat generating thermistors, heat the nearby gas. In the case of oxygen, the paramagnetic properties decrease with heat causing gas flow away from the gas concentration surrounding the high-intensity magnetic field. This generates a gas flow in the direction of the adjacent thermistors of each pair located outside the magnetic field, i.e. heat sensing thermistors R1 and R2. Thus, the heat generating thermistors W1 and W2, lose heat to the adjacent thermistors R1 and R2 of each pair. The presence of oxygen in the oxygen sensing cell 100 tends, then, to proportionally reduce the temperature of the heat generating thermistors W1 and W2 because of a cooling effect of the "wind," and tends to increase the temperature of the adjacent thermistors R1 and R2.

Figure 2:
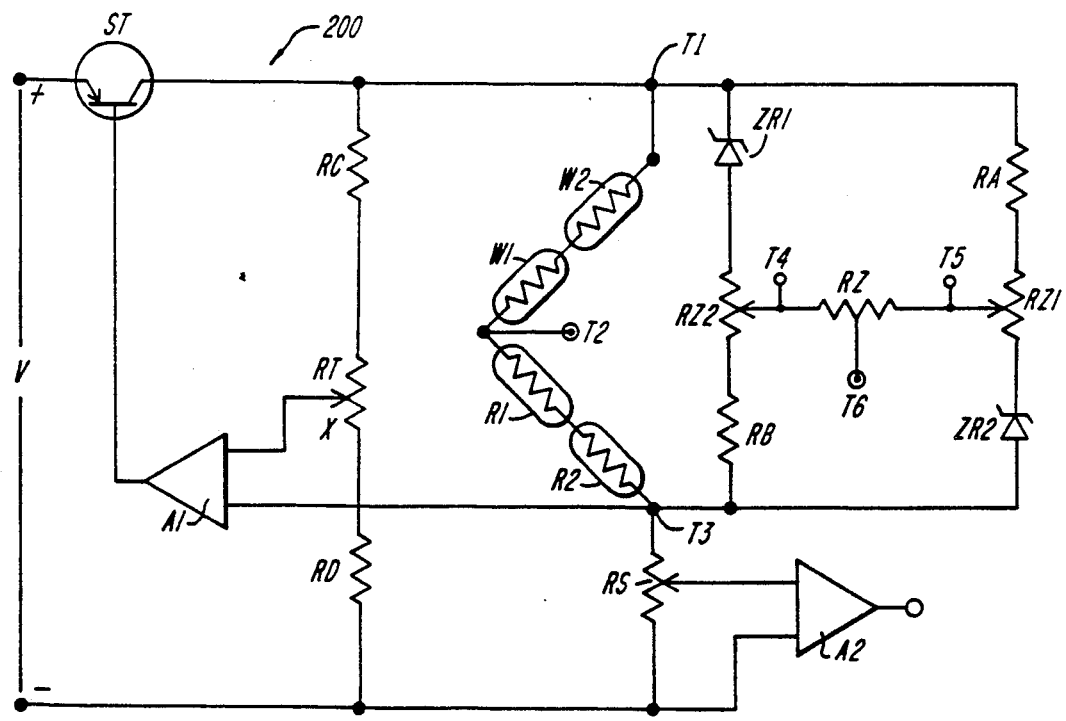
FIG. 2 is a schematic diagram depicting a sensing bridge circuit in accordance with the principal of this invention.

In a preferred embodiment of the present invention, as illustrated in FIG. 2, the thermistor pair W1 and W2 is serially connected between terminals T1 and T2 and thermistors R1 and R2 are connected between terminals T2 and T3. The measuring bridge circuit 200 is unbalanced, due to the resistance change resulting from the thermistor temperature unbalance. This thermistor temperature unbalance, in turn, is proportional to oxygen concentration.

The circuit illustrated in FIG. 2 eliminates the undesirable effects of ambient temperature variations by controlling the temperature of the heat generating elements W1 and W2. The temperature of sensing elements R1 and R2 is maintained at a substantially constant level by a feedback high precision temperature control loop which includes the illustrated series transistor ST and bridge temperature adjusting element RT. In particular, the illustrated circuit 200 includes a constant temperature bridge, formed by resistors RC, RD, RS, and a measuring bridge consisting of thermistors W1, W2, R1, R2, resistances RA, RB, RZ, RZ1, RZ2, and Zener diodes ZR1 and ZR2. These Zener diodes are non-linear elements exhibiting a substantially non-linear voltage-current characteristic over a substantial range of current values.

Potentiometer RT is utilized as a bridge temperature adjustment element. Comparator amplifier A1, which can be of conventional design and construction, detects any electrical unbalance between node "X" and terminal T3 and drives the series transistor ST to change the voltage between terminals T1 and T3 so as to restore the bridge balance. A temperature control circuit of this type may be found in U.S. Pat. No. 4,893,495.

This detection and control loop maintains the elements of the measuring bridge at constant temperature, regardless of any variation in background gas composition that would otherwise affect, through changes in thermal conductivity and paramagnetism, the thermistor heat dissipation and temperature. The optimum temperature of the thermistors, in the absence of oxygen, has been found to be approximately 200° C.

Another feature of the illustrated configuration is the ability to obtain a signal, at the output of amplifier A2, which can be used as a correction signal, or multiplier, for accurately correcting the oxygen reading obtained from the measuring bridge. This signal is obtained by sensing through RS the current change necessary to restore the bridge balance. This is also discussed in the above referenced patent.

Figure 3:
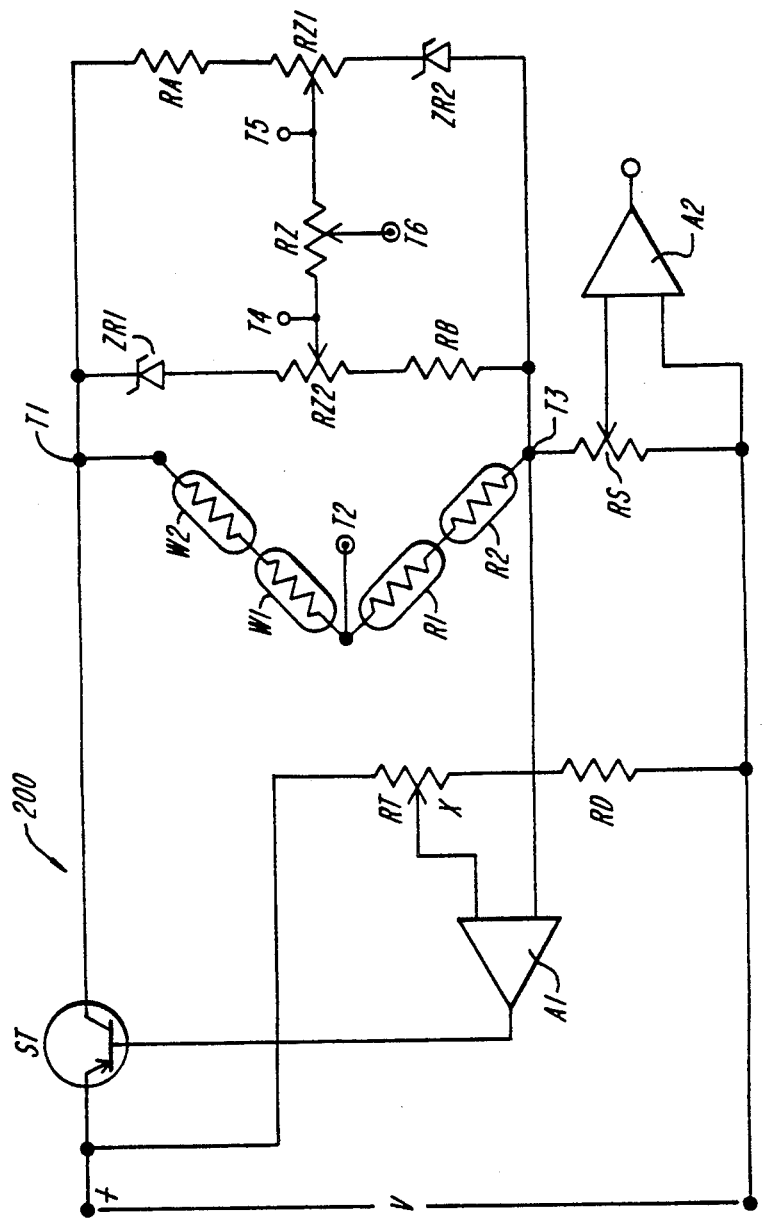
FIG. 3 is a schematic diagram of a second embodiment of a sensing bridge circuit in accordance with the principals of this invention.

As illustrated in FIG. 3, a variation on this detection and control loop provides for maintaining a constant current through the elements of the measuring bridge rather than maintaining these elements at constant temperature. In this configuration, one end of resistor RT is connected to a constant voltage source, so that the input of amplifier A1 is driven to maintain the current through the elements W1, W2, R1 and R2 constant.

The oxygen measuring bridge is also a bridge within a bridge. The first side of an outer bridge is formed by the thermistors W1, W2, R1, R2. The second side of the bridge is actually an inner bridge. The first side of the inner bridge is a serial combination of elements ZR1, RZ2 and RB. The second side of the inner bridge is a serial combination of RA, RZ1, and ZR2. The diode ZR1 is connected between terminal T1 and one end of potentiometer RZ2, while the diode ZR2 is connected between terminal T3 and one end of potentiometer ZR1. The two sides are connected at terminals T4 and T5 by potentiometer RZ, having its adjustable tap connected to terminal T6. The output signal indicating the concentration of oxygen in the gas mixture is read between terminals T2 and T6.

This bridge within a bridge design allows a user to negate any thermal or paramagnetic characteristics of two or more background gases. In the case of two background gases, each gas is placed in the chamber, one at a time, and the circuit is adjusted to remove from an oxygen measurement the contribution of each background gas. If more than two background gases are present, choosing from among them two gases that represent opposite extremes in terms of thermal and paramagnetic properties allows the circuit to perform measurements with a high degree of accuracy without having to balance the circuit for each individual gas.

The dynamics of how the circuit performs these tasks are explained in the following example. In the example, values will be specified for circuit elements. One skilled in the art will realize that these values are illustrative but may vary in practice.

In this example the percentage of oxygen in a gas mixture of nitrogen, hydrogen, and oxygen is to be measured. The chamber containing the oxygen sensor is first filled with 100% nitrogen. The thermal transfers properties of the gas results in a change in the sensed temperature at the sensing thermistors, R1 and R2. The change causes an adjustment in the voltage exhibited between terminals T1 and T3. This voltage results from the actions of the voltage control circuit RT, RC, RD and A1, which adjusts the voltage generated by ST to maintain a constant temperature at thermistors R1 and R2. The voltage generated by ST may range from 0 to 24 volts. In the case of nitrogen, the input voltage with respect to ground is typically 8.2 volts.

In a first zero calibration step, with only nitrogen in the chamber, a voltage appears between terminals T1 and T3 representative of the aforementioned properties of nitrogen. This voltage is then used as a reference voltage for balancing the circuit. A volt meter is placed between the terminal T4, and terminal T2. RZ2 is a potentiometer, having a resistance of five hundred ohms with its arm connected to terminal T4. The position of the potentiometer arm is adjusted until there is zero potential between terminal T4 and terminal T2.

Next, the same operation is performed by zeroing the potential between terminal T5 and terminal T2 by adjustment of the arm of potentiometer RZ1. RZ1 is likewise a 500 ohm potentiometer, the arm of which is connected to terminal T5. This has minimal effect on the balancing which has already occurred between terminal T4 and terminal T5 because of the relatively high impedance value between terminal T4 and terminal T5. This value is embodied in potentiometer RZ, which has a value of approximately 20 kilohms. If the balancing between T4 and T5 is affected, even minimally, this can be corrected by repeating the step of zeroing the voltage between terminals T4 and T5.

With the two sets of terminals so balanced there exists a balance between terminal T6 of the arm of potentiometer RZ, and terminal T2.

The nitrogen is then flushed from the chamber which is then filled with the second background gas, hydrogen, for a second zero calibration step. The previously discussed temperature control dynamic occurs reflecting the thermal transfer characteristic of hydrogen altering the output voltage from transistor ST to about 16.4 volts.

The voltage at terminal T2 responds with an appropriate increase causing again an imbalance between the two bridges.

A typical Wheatstone Bridge, once in a balanced condition, responds to changes in input voltage by distributing the voltage drops proportionally among its resistive elements. This characteristic ensures that the bridge remains balanced.

However, the inner bridge, which has non-linear voltage elements, ZR1 and ZR2 does not react the same way. When the voltage across the terminals T1 and T3 increases, the voltage drop across diode ZR1 remains essentially unchanged. This drop is limited because of the properties of ZR1, a Zener diode. In the preferred embodiment, ZR1 ensures that the voltage drop does not exceed 1.2 volts. Likewise, another Zener diode ZR2 is located below RZ1 restricting the voltage drop across that diode to a predetermined amount. This amount would also usually not exceed 1.2 volts.

It is easily seen that Kirchhoff's voltage law dictate that an imbalance is now created between terminals T4 and T5. This, of course, results in an imbalance between terminal T2 and terminal T6. Adjusting the position of the tap on potentiometer RZ alters the voltage at terminal T6 such that the bridge becomes balanced for the second background gas, hydrogen.

It should be noted that potentiometers RZ1 and RZ2 were not adjusted for hydrogen. Therefore, if hydrogen and/or nitrogen were introduced to the chamber, the voltage between terminals T2 and T6 would remain zero. Therefore, the bridge would be balanced under either condition.

The gas mixture to be tested is now placed in the chamber. The background gases' characteristics have essentially been compensated by the inner bridge. The voltage difference between terminals T2 and T6 is then proportional to the oxygen content within the chamber.

It will be understood that changes may be made in the above construction and in the foregoing sequences of operation without departing from the scope of the invention. It is accordingly intended that all matter contained in the above description or shown in the accompanying drawings be interpreted as illustrative rather than in a limiting sense.

It is also to be understood that the following claims are intended to cover all of the generic and specific features of the invention as described herein, and all statements of the scope of the invention which, as a matter of language, might be said to fall therebetween.

What is claimed is:

1. In a measurement system for determining a variable component of a thermally conductive medium having first and second background components, where said system comprises,
   an electrical resistive heat generating network contributing heat to said medium, connected between a first terminal and a second terminal,
   an electrical resistive heat sensing network, sensing heat in said medium connected between said second terminal and a third terminal,
   a voltage generator for producing a voltage between said first and third terminals,
   feedback voltage control means for controlling the voltage produced by said voltage generator to maintain the temperature at said heat sensing network substantially constant,
   said thermally conductive medium thermally coupling said heat generating network and said heat sensing network,
   the improvement comprising,
   a background compensation circuit connected between said first and said third terminals, said background compensation circuit including,
   a first series circuit having a first non-linear element exhibiting a non-linear voltage-current characteristic over a substantial range of current values, a first adjustable tap resistor connected in series between said first and said third terminals, said first non-linear element being connected between said first terminal and one end of said first adjustable tap resistor,
   a second series circuit having a second adjustable tap resistor and a second non-linear element exhibiting a non-linear voltage-current characteristic over a range of current values, connected in series between said first terminal and said third terminal, said second non-linear element being connected to said third terminal and one end of said second adjustable tap resistor,
   an adjustable position tap on said first adjustable resistor being connected to a fourth terminal, an adjustable position tap on said second adjustable resistor being connected to a fifth terminal,
   a third adjustable tap resistor connected between said fourth terminal and said fifth terminal, an adjustable tap of said third adjustable tap resistor being connected to a sixth terminal,
   wherein the voltage at said fourth terminal can be adjusted to be equal to the voltage at said second terminal and the voltage at said fifth terminal can be adjusted to be equal to the voltage at said fourth terminal and said second terminal, under the condition where only one background component of said thermally conductive medium is present in a first calibration step, and the voltage at said sixth terminal can be adjusted to be equal to the voltage of said second terminal under a condition where only said second background component is present, in a second calibration step, the voltage between said second terminal and said sixth terminal is indicative of the concentration of said variable component, when said thermally conductive medium includes said variable component together with said first and second background components.

2. Apparatus in accordance with claim 1 wherein first and second non-linear elements are Zener diodes exhibiting a region of substantially constant voltage output for a range of current inputs.

3. An apparatus in accordance with claim 1 wherein said voltage generator is a series transistor.

4. Apparatus in accordance with claim 1 wherein said feedback voltage control means comprises a comparator amplifier having first and second inputs and providing an output signal in response to the difference in voltage between said first and second inputs, one of said inputs being connected to said third terminal,
   the other of said comparator amplifier inputs being connected to an adjustable point of potential reference, which is set at a reference value to produce a selected value of temperature across said heat generating network, the output of said comparator amplifier being connected as a control signal to said voltage generator.

5. Apparatus in accordance with claim 1 wherein said thermally conductive medium is a gas mixture including a specific gas as a variable component and at least two specific gases as background components.

6. Apparatus in accordance with claim 2 and further including resistive elements connected in parallel with said Zener diodes to control the range of operation of said Zener diodes.

7. An apparatus in accordance with claim 1 wherein said apparatus is for measuring a concentration of a paramagnetic gas in a gas mixture, said apparatus further including means for generating a high intensity non-uniform magnetic field around said gas mixture, wherein said heat generating network is located at a first position within said high intensity non-uniform magnetic field and said heat sensing network is located at a second position outside said high intensity non-uniform magnetic field, and wherein the ratio of the resistive value of said heat generating network to the resistive value of said heat sensing network varies in proportion to the concentration of said paramagnetic gas.

8. In a measurement system for determining a variable component of a medium having first and second background components, where said system comprises,
   an electrical energy generating network connected between a first terminal and a second terminal,
   an electrical energy sensing network sensing the energy in said medium at said sensing network, connected between said second terminal and a third terminal,
   a voltage generator for producing a voltage between said first and third terminals,
   feedback voltage control means for controlling the voltage produced by said voltage generator to maintain the energy level at said energy sensing network substantially constant,
   said medium coupling energy from said energy generating network to said heat sensing network,
   the improvement comprising, a background compensation circuit connected between said first and said third terminals, said background compensation circuit including, a first series circuit having a first non-linear element exhibiting a non-linear voltage-current characteristic over a substantial range of current values, a first adjustable tap resistor connected in series between said first and said third terminals, said first non-linear element being connected between said first terminal and one end of said first adjustable tap resistor, a second series circuit having a second adjustable tap resistor and a second non-linear element exhibiting a non-linear voltage-current characteristic over a range of current values, connected in series between said first terminal and said third terminal, said second non-linear element being connected between said third terminal and one end of said second adjustable tap resistor, an adjustable position tap on said first adjustable resistor being connected to a fourth terminal, an adjustable position tap on said second adjustable resistor being connected to a fifth terminal, a third adjustable tap resistor connected between said fourth terminal and said fifth terminal, an adjustable tap of said third adjustable tap resistor being connected to a sixth terminal, wherein the voltage at said fourth terminal can be adjusted to be equal to the voltage at said second terminal and the voltage at said fifth terminal can be adjusted to be equal to the voltage at said fourth terminal and said second terminal, under the condition where only one background component of said thermally conductive medium is present in a first calibration step, and the voltage at said sixth terminal can be adjusted to be equal to the voltage of said second terminal under the condition where only said second background component is present, in a second calibration step, the voltage between said second terminal and said sixth terminal is indicative of the concentration of said variable component when said thermally conductive medium includes said variable component together with said first and second background components.

9. An improved method for determining a variable component of a thermally conductive medium having first and second background components, where said method comprises the steps of, heating a first resistive network connected between a first terminal and a second terminal to produce heat in said medium, sensing heat in said medium at a second resistive network connected between said second terminal and a third terminal, producing a voltage between said first and third terminals, controlling the voltage produced by said voltage generator to maintain the temperature at said second resistive network substantially constant, thermally coupling said heat generating network and said heat sensing network, the improvement comprising the steps of, establishing a background compensation circuit connected between said first and said third terminals, said background compensation circuit including, a first series circuit having a first non-linear element exhibiting a non-linear voltage-current characteristic over a substantial range of current values, a first adjustable tap resistor connected in series between said first and said third terminals, said first non-linear element being connected between said first terminal and one end of said adjustable tap resistor, a second series circuit having a second adjustable tap resistor and a second non-linear element exhibiting a non-linear voltage-current characteristic over a range of current values, connected in series between said first terminal and said third terminal, said second non-linear element being connected between said third terminal and one end of said second adjustable tap resistor, an adjustable tap position tap on said first adjustable tap resistor being connected to a fourth terminal, an adjustable tap position on said adjustable tap resistor being connected to a fifth terminal, a third adjustable tap resistor connected between, said fourth terminal and said fifth terminal, an adjustable tap of said third adjustable tap resistor being connected to a sixth terminal, adjusting the voltage at said fourth terminal to be equal to the voltage at said second terminal, adjusting the voltage at said fifth terminal to be equal to the voltage at said fourth terminal and said second terminal, under a condition where only one background component of said thermally conductive medium is present, and adjusting the voltage at said sixth terminal to be equal to the voltage of said second terminal under a condition where only said second background component is present, measuring the voltage between said sixth terminal and said second terminal as indicative of the concentration of said variable component when said medium includes said variable component of said first and second background components.

10. In a measurement system for determining a variable component of a thermally conductive medium having first and second background components, where said system comprises, an electrical resistive heat generating network contributing heat to said medium, connected between a first terminal and a second terminal, an electrical resistive heat sensing network, sensing heat in said medium connected between said second terminal and a third terminal, a voltage generator for producing a voltage between said first and third terminals, feedback voltage control means for controlling the voltage produced by said voltage generator to maintain the current through said heat generating and said heat sensing network substantially constant, said thermally conductive medium thermally coupling said heat generating network and said heat sensing network, the improvement comprising, a background compensation circuit connected between said first and said third terminals, said background compensation circuit including, a first series circuit having a first non-linear element exhibiting a non-linear voltage-current characteristic over a substantial range of current values, a first adjustable tap resistor connected in series between said first and said third terminals, said first non-linear element being connected between said first terminal and one end of said first adjustable tap resistor.

a second series circuit having a second adjustable tap resistor and a second non-linear element exhibiting a non-linear voltage-current characteristic over a range of current values, connected in series between said first terminal and said third terminal, said second non-linear element being connected to said third terminal and one end of said second adjustable tap resistor, an adjustable position tap on said first adjustable resistor being connected to a fourth terminal, an adjustable position tap on said second adjustable resistor being connected to a fifth terminal, a third adjustable tap resistor connected between said fourth terminal and said fifth terminal, an adjustable tap of said third adjustable tap resistor being connected to a sixth terminal, wherein the voltage at said fourth terminal can be adjusted to be equal to the voltage at said second terminal and the voltage at said fifth terminal can be adjusted to be equal to the voltage at said fourth terminal and said second terminal, under the condition where only one background component of said thermally conductive medium is present in a first calibration step, and the voltage at said sixth terminal can be adjusted to be equal to the voltage of said second terminal under a condition where only said second background component is present, in a second calibration step, the voltage between said second terminal and said sixth terminal is indicative of the concentration of said variable component, when said thermally conductive medium includes said variable component together with said first and second background components.

11. In a measurement system for determining a variable component of a medium having first and second background components, where said system comprises, an electrical, energy generating network connected between a first terminal and a second terminal, an electrical, energy sensing network sensing the energy in said medium at said sensing network, connected between said second terminal and a third terminal, a voltage generator for producing a voltage between said first and third terminals, feedback voltage control means for controlling the voltage produced by said voltage generator to maintain the current through said energy generating and said energy sensing network substantially constant, said medium coupling energy from said energy generating network to said heat sensing network, the improvement comprising, a background compensation circuit connected between said first and said third terminals, said background compensation circuit including, a first series circuit having a first non-linear element exhibiting a non-linear voltage-current characteristic over a substantial range of current values, a first adjustable tap resistor connected in series between said first and said third terminals, said first non-linear element being connected between said first terminal and one end of said first adjustable tap resistor, a second series circuit having a second adjustable tap resistor and a second non-linear element exhibiting a non-linear voltage-current characteristic over a range of current values, connected in series between said first terminal and said third terminal, said second non-linear element being connected between said third terminal and one end of said second adjustable tap resistor, an adjustable position tap on said first adjustable resistor being connected to a fourth terminal, an adjustable position tap on said second adjustable resistor being connected to a fifth terminal, a third adjustable tap resistor connected between said fourth terminal and said fifth terminal, an adjustable tap of said third adjustable tap resistor being connected to a sixth terminal, wherein the voltage at said fourth terminal can be adjusted to be equal to the voltage at said second terminal and the voltage at said fifth terminal can be adjusted to be equal to the voltage at said fourth terminal and said second terminal, under the condition where only one background component of said thermally conductive medium is present in a first calibration step, and the voltage at said sixth terminal can be adjusted to be equal to the voltage of said second terminal under the condition where only said second background component is present, in a second calibration step, the voltage between said second terminal and said sixth terminal is indicative of the concentration of said variable component when said thermally conductive medium includes said variable component together with said first and second background components.

12. An improved method for determining a variable component of a thermally conductive medium having first and second background components, where said method comprises the steps of, heating a first resistive network connected between a first terminal and a second terminal to produce heat in said medium, sensing heat in said medium at a second resistive network connected between said second terminal and a third terminal, producing a voltage between said first and third terminals, controlling the voltage produced by said voltage generator to maintain the current through said first resistive network and said second resistive network substantially constant, thermally coupling said heat generating network and said heat sensing network, the improvement comprising the steps of, establishing a background compensation circuit connected between said first and said third terminals, said background compensation circuit including, a first series circuit having a first non-linear element exhibiting a non-linear voltage-current characteristic over a substantial range of current values, a first adjustable tap resistor connected in series between said first and said third terminals, said first non-linear element being connected between said first terminal and one end of said adjustable tap resistor, a second series circuit having a second adjustable tap resistor and a second non-linear element exhibiting a non-linear voltage-current characteristic over a range of current values, connected in series between said first terminal and said third terminal, said second non-linear element being connected between said third terminal and one end of said second adjustable tap resistor, an adjustable position tap on said first adjustable tap resistor being connected to a fourth terminal, an adjustable position tap on said second adjustable tap resistor being connected to a fifth terminal, a third adjustable tap resistor connected between said fourth terminal and said fifth terminal, an adjustable tap of said third adjustable tap resistor being connected to a sixth terminal, adjusting the voltage at said fourth terminal to be equal to the voltage at said second terminal, adjusting the voltage at said fifth terminal to be equal to the voltage at said fourth terminal and said second terminal, under a condition where only one background component of said thermally conductive medium is present, and adjusting the voltage at said sixth terminal to be equal to the voltage of said second terminal under a condition where only said second background component is present, measuring the voltage between said sixth terminal and said second terminal as indicative of the concentration of said variable component when said medium includes said variable component of said first and second background components.

* * * * *